(12) United States Patent
Sims et al.

(10) Patent No.: US 7,179,089 B2
(45) Date of Patent: Feb. 20, 2007

(54) ABUTMENT SYSTEM AND METHOD FOR PREPARING THE SAME

(75) Inventors: Lawrence O. Sims, Alpharetta, GA (US); Brian K. Lindke, Buford, GA (US); Yuichi Ikenaga, Buford, GA (US)

(73) Assignee: Prosthosolve, LLC, Buford, GA (US)

( * ) Notice: Subject to any disclaimer, the term of this patent is extended or adjusted under 35 U.S.C. 154(b) by 216 days.

(21) Appl. No.: 10/689,179

(22) Filed: Oct. 20, 2003

(65) Prior Publication Data

US 2005/0084819 A1    Apr. 21, 2005

(51) Int. Cl.
   *A61C 8/00*    (2006.01)
(52) U.S. Cl. .................. 433/173; 433/172; 433/174; 433/175; 433/201.1
(58) Field of Classification Search ............. 433/173, 433/201.1, 212.1, 202.1, 204, 172, 174, 175
See application file for complete search history.

(56) References Cited

U.S. PATENT DOCUMENTS

| | | | | |
|---|---|---|---|---|
| 4,689,013 | A * | 8/1987 | Lustig ..................... 433/181 |
| 5,321,053 | A | 6/1994 | Hino et al. |
| 5,346,397 | A * | 9/1994 | Braiman ................... 433/223 |
| 5,683,249 | A * | 11/1997 | Ibsen et al. ............. 433/201.1 |
| 5,759,036 | A * | 6/1998 | Hinds ...................... 433/173 |
| 6,024,567 | A * | 2/2000 | Callan ..................... 433/173 |
| 6,267,597 | B1 * | 7/2001 | Kim ........................ 433/224 |
| 6,497,573 | B2 | 12/2002 | Wagner et al. |
| 6,607,386 | B1 * | 8/2003 | Andersson et al. ...... 433/201.1 |
| 6,648,645 | B1 * | 11/2003 | MacDougald et al. ...... 433/223 |
| 2002/0025506 | A1 * | 2/2002 | Hagenbuch et al. ..... 433/201.1 |
| 2002/0197583 | A1 * | 12/2002 | Jones et al. ............. 433/202.1 |
| 2004/0063070 | A1 * | 4/2004 | Morgan .................... 433/173 |

OTHER PUBLICATIONS

Kurraray Medical Inc: ESTENIA Data Sheet—Published no later than Sep. 13, 2001.
Kurraray Dental: Panavia brochure—Publishe Jul. 2001.
Department of Bioengineering—Imperial College of Scehnce Technology & Medicine: "Dental Composites"—2002.

(Continued)

Primary Examiner—Melba N. Bumgarner
Assistant Examiner—Jonathan Werner
(74) Attorney, Agent, or Firm—Bryan W. Bockhop; Bockhop & Associates, LLC

(57) ABSTRACT

An abutment system for a dental implant includes an abutment having a base portion that is engageable with a dental implant and a shoulder disposed about the base portion that includes a hybrid ceramic material. The hybrid ceramic material includes at least 85% porcelain. An opaque can be applied to the exterior surface of the abutment. A pigment can also be added to the hybrid ceramic material so as to match the color of the patient's gum tissue. A method of preparing an abutment system includes the steps of forming a curable hybrid ceramic material into a shoulder about the base portion of an abutment, partially curing the hybrid ceramic material so as to form an initially cured shoulder, shaping the initially cured shoulder to a desired shape so that the shoulder conforms to at least one patient specific criterion, and completely curing the shoulder. A plurality of abutment systems may be assembled into a kit.

12 Claims, 6 Drawing Sheets

OTHER PUBLICATIONS

Dagani: "Putting the 'Nano' into Composites"—C&EN, Jun. 7, 1999, p. 25.
Novak; "Hybrid Nanocomposite Materials—Between Inorganic Glasses and Organic Polymers" Adv. Matter—1993, p. 422.

Hara et al.: "Radiopacity of Glass-Ionomer/Composite Resin Hybrid Materials" Braz. Dent. J., 2001.
Wel et al.: "A New Class of Organic-Inorganic Hybrid Dental Materials" Poly. Prep. 1997.

* cited by examiner

ABUTMENT SYSTEM AND METHOD FOR PREPARING THE SAME

BACKGROUND OF THE INVENTION

1. Field of the Invention

The present invention relates to abutments used in implant dentistry and, more specifically, to an abutment system having an abutment with a shoulder that includes a hybrid ceramic material. The present invention also relates to a comprehensive abutment try-in protocol for determining correct abutment selection, including specifically an abutment to be chosen and placed at the time of first stage implant surgery, also known as an immediate load abutment, and hybrid ceramic temporary shells for the purpose of fabricating immediate load temporaries at the first stage surgical appointment of implant placement.

2. Description of the Prior Art

When a permanent crown is installed in a patient's mouth, the procedure that is generally followed is that an implant is first surgically placed into the patient's jawbone, and the crown is affixed to the implant device by use of an abutment, which is a substantially cylindrical device that is typically screwed into the implant, and the crown is then affixed on top of the abutment. It is well known in the art that a shoulder can be affixed to or shaped on the base portion of the abutment. The purpose of the shoulder is to provide a more seamless transition between the abutment and the gum tissue. Ideally the shoulder rests just below the crest of the gum tissue.

There are many problems and difficulties associated with the current state of implant dentistry. First, when a permanent crown is going to be implanted, an impression of the patient's mouth, which will be used to create the abutment system and the crown, is taken in the dentist's office, and then sent to a dental laboratory, and the dental laboratory manufactures the crown. Because gum tissue changes over time, by the time the dental laboratory manufactures the abutment system and the crown and sends them back to the dentist to be affixed in the patient's mouth, the dimensions of the patient's mouth, in particular the shape of the gum tissue, will likely have changed. Therefore, the abutment system and/or the crown may no longer fit as well into the patient's mouth. As a result, the crown may not appear natural in the patient's mouth. For example, there may be a gap, or margin, between the base of the crown and the patient's gum line, such that the base portion of the abutment is visible. This is highly undesirable, particularly because the abutment is usually manufactured from a metal substance. This is also problematic because, once the shoulder has been formed about the base of the abutment, it can be reduced in size, such as by grinding it down, but no material can be added to it in order to shape it to better fit in the patient's mouth. Rather, an entirely new abutment system has to be made.

Another problem associated with implant dentistry arises when a small tooth is being replaced with a permanent crown. When a small tooth is replaced, the permanent crown likewise must be very small. Because the abutment is of a predetermined width, the permanent crown will be very thin. As the crown is made of porcelain, it is very fragile. The thinner the crown, the more fragile it is. Thin crowns have a tendency to break. If a portion of the crown breaks off when the dentist is affixing it in the patient's mouth, the dentist must request that the dental laboratory manufacture another crown. This results in additional time during which the patient must wait for the permanent crown to be affixed.

Another problem associated with implant dentistry is that some patients are sensitive to the toxicity of the acrylic monomers that are present in the materials that are commonly used as components of the materials that are used to form the shoulder about the base portion of the abutment, as well as the crown. If a patient has a reaction to the acrylic monomers that are present in the crown or the shoulder, this will compromise the healing of the gum tissue after the crown is affixed, and may require removal of the crown and the abutment system.

Another problem with crowns is the difficulty they have in duplicating the appearance of a natural tooth. As they are currently made, the composition of porcelain and acrylic material that is used to make the crown is not highly polishable. As a result, it is difficult to make the permanent crown have the appearance of a natural tooth. Another problem associated with dental implants is lack of light transmission into the soft tissue surrounding the implant. This causes a graying of the tissue directly around the implant because metal, pure zirconia and aluminous oxide abutments cannot transmit light.

Another problem associated with dental implants is that the implant fixture is frequently placed in the bone at an angle that makes it extremely difficult to restore with currently available abutments. The fixture may be angled towards the buccal, the lingual or interproximals. The fixture is also frequently positioned too high or too low in relation to the bone and/or gum tissue.

Another problem associated with dental implants is the temporization of temporary or permanent implant abutments. Implant abutments are frequently placed at an angle that precludes the use of traditional temporary crowns. Temporization is further complicated if attempted at the time of first stage surgery, as in an immediate load situation. Another problem associated with dental implants is the inability to load the implant fixture at the time of first stage surgery. This requires the use of a permanent abutment and a temporary crown. Fabricating and placing temporaries at this surgery is not a common procedure and requires a great deal of time as well as the use of traditional temporary modalities which are very impractical for this procedure. This procedure is also very time-consuming and not very cost effective.

Another problem associated with dental implants is that the materials that are commonly used to form the shoulder about the base of the abutment may not be compatible with all metals. Therefore, the material that can be selected to form the shoulder may be limited by the compatibility of that material with the type of metal that was used to create the abutment.

Another problem associated with current abutment systems is that the material used to form the shoulder about the base of the abutment may not be biocompatible with the patient's gum tissue, thereby hindering the healing process once the crown has been affixed. If the gum tissue does not heal properly around the implant and abutment system, infection and gum tissue loss can result.

Another problem associated with dental implants is the inability to select the final abutment by the surgeon and restorative dentists. The dental laboratory typically decides what the configuration of the abutment will be by analyzing the plaster impressions taken of the patient's mouth. This prevents the surgeon or restorative dentist from being able to observe and possibly correct any angle problem or tissue height discrepancy.

SUMMARY OF THE INVENTION

The disadvantages of the prior art are overcome by the present invention, which in one aspect, is an abutment system. In the abutment system, the abutment has a shoulder disposed about the base of the abutment. The abutment is an opaqued metal cylinder, an aluminous oxide cylinder, a tooth colored fiber reinforced cylinder, or a pure zirconia cylinder that is affixed to the implant fixture by a screw. The shoulder includes a hybrid ceramic material. The hybrid ceramic material includes at least 85% porcelain, and preferably includes at least 92% porcelain. The characteristics of the hybrid ceramic material allow a shoulder to be modified after the shoulder has already been formed, including allowing for additional hybrid ceramic material to be added onto the already existing shoulder. This is highly advantageous, because it allows the oral surgeon or restorative dentist to modify the abutment at any time so as to allow for the ideal shape, contour, and margin placement. This is accomplished by either adding to or reducing the shoulder area of the abutment. This can be done in the dentist's office rather than having to send the abutment system back to the dental laboratory for adjustment. This also results in minimal to no margin existing between the gum tissue and the crown once it is installed.

Another advantage of the present invention is the ability to correct the divergent angle created by the implant fixture. Not only can the length of the abutment be modified, the shoulder can be reconfigured to accommodate any angulation problem. Shoulder height, width, and emergence profile can all be added to or reduced to exact size and shape.

The ability to add hybrid ceramic material to the shoulder even after it is formed overcomes the problems associated with crowns that break in the dentist's office. If a crown breaks, the dentist can add hybrid ceramic material to the abutment system in the place of the broken portion of the crown. This is an acceptable solution because the hybrid ceramic material is highly polishable and is transluminescent, and therefore has the appearance of a natural tooth, including below the gum line. Hybrid ceramic materials have the ability to transmit light from the margin/shoulder area to beneath the gum tissue. This light transmission has never been accomplished to such a high degree with previous abutment shoulder materials. This ability to transmit light eliminates the traditional graying of the tissue surrounding the implant.

Another advantage of the present invention is that the hybrid ceramic material is highly biocompatible. Gum tissue that is in contact with the hybrid ceramic material responds well and heals at a predictable rate. The success of the abutment system and crown is enhanced by the very low risk of a negative reaction to any monomers that might be present in the hybrid ceramic material. Because the hybrid ceramic material includes a very low percentage of acrylic monomer initially, the risk of a negative reaction is reduced. The risk is further reduced because the final curing step of the method of making the abutment system entails exposing the abutment system to heat, which drives off any additional remaining monomer in the hybrid ceramic material.

Another advantage of the present invention is that the hybrid ceramic material is compatible with all metals that are used for abutments, thereby eliminating this concern.

Another advantage of the present invention is that the shoulder can be formed about the abutment so that the shoulder extends out over a portion of the gum tissue, which, when pigment is added to the hybrid ceramic material that extends out over the gum tissue, creates the appearance of additional gum tissue. This is not only aesthetically desireable in some cases, as it creates a uniform appearance to the gum tissue, it can aid the regeneration of the actual gum tissue due to the reduced size of the biological width.

These and other aspects of the invention will become apparent from the following description of the preferred embodiments taken in conjunction with the following drawings. As would be obvious to one skilled in the art, many variations and modifications of the invention may be affected without departing from the spirit and scope of the novel concepts of the disclosure.

DETAILED DESCRIPTION OF THE INVENTION

Figure 1:
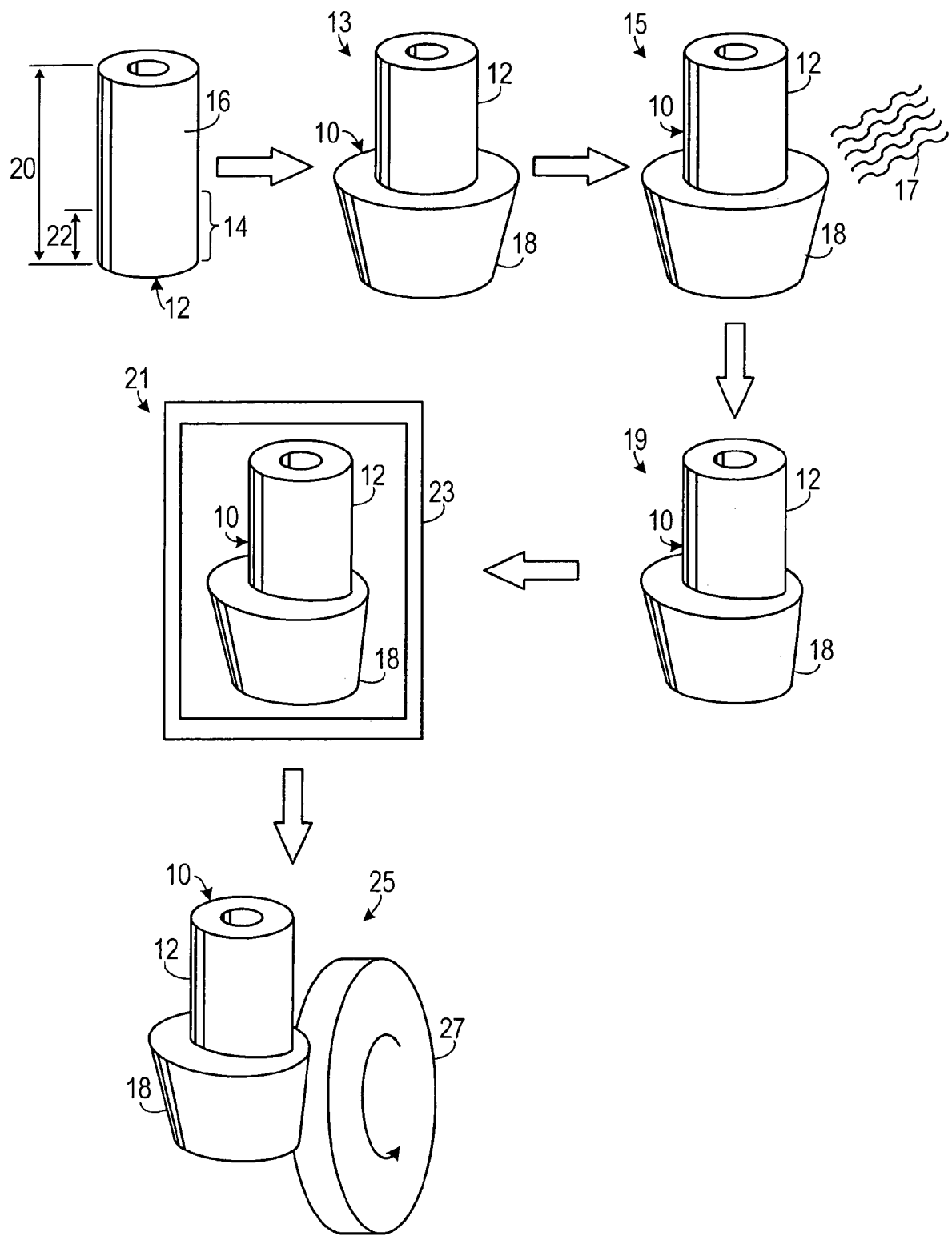
FIG. 1 is a diagram that demonstrates a method of making the abutment system disclosed herein.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

A method for making an abutment system is shown in FIG. 1. After an impression is taken of the patient's mouth and the appropriate criteria for making the abutment system 10 are determined, an abutment 12 is selected according to those patent specific criteria. The abutment 12 has a base portion 14. In a preferred method for making the abutment system 10, an opaque is applied to at least a portion of the exterior surface 16 of the abutment 12. A shoulder 18 is formed 13 about the base portion 14 of the abutment 12 using a hybrid ceramic material. In a preferred method for making an abutment system, the hybrid ceramic material includes at least 85% porcelain. In a particularly preferred embodiment, the hybrid ceramic material includes at least 92% porcelain. One such hybrid ceramic material that can be used is Estenia®, which is manufactured by Kuraray, a Japanese corporation that manufactures adhesive dental products. The shoulder 18 is formed about the base portion 14 of the abutment 12 using various hand tools, preferably spatulas and brushes. The hybrid ceramic material may be formed about the entire length 20 or a portion of the length 22 of the abutment 12 so as to change or alter the angulation and color of the abutment 12. The hybrid ceramic material shoulder can be constructed onto either an opaque metal cylinder abutment or a zirconia or alumina cylinder abutment. A zirconia cylinder abutment will transmit even more light than the opaque metal cylinder abutment. The present invention can also be utilized with all standard fixture platforms currently available.

In another embodiment of the present invention, where an aluminous oxide abutment or zirconia abutment is used, a ceramic foundation layer is applied to the portion of the abutment 12 about which the shoulder 18 will be formed. This procedure assures a chemical as well as mechanical adhesion of the hybrid ceramic material to the abutment 12. This ceramic foundation layer may also incorporate the use of a pigment to further enhance the final appearance of the shoulder 18.

Once the shoulder 18 is formed about the base portion 14 of the abutment 12, the shoulder 18 is initially cured 15. In a preferred embodiment of the present invention, the shoulder 18 is cured by exposing the shoulder 18 to ultraviolet light 17. In one embodiment of the invention, the shoulder 18 is exposed to a high intensity ultraviolet light source by placing the abutment system 10 in a typical dental curing unit. In another embodiment of the invention, the shoulder 18 is exposed to ultraviolet light by the dentist using a hand-held high intensity ultraviolet light source.

Once the shoulder 18 is initially cured, the shoulder 18 is shaped 19 so as to conform to at least one patient specific criterion. In one embodiment of the invention, additional hybrid ceramic material is added to the shoulder 18 so as conform the shoulder 18 to at least one patient specific criterion. For example, additional hybrid ceramic material can be added to the shoulder 18 so as to increase its height 24. In another embodiment of the invention, hybrid ceramic material is removed from the shoulder 18 so as to conform the shoulder 18 to at least one patient specific criterion. For example, hybrid ceramic material can be sanded or ground from the shoulder 18 so as to decrease its widths 26a and/or 26b. In an alternative embodiment of the invention, the shoulder 18 is conformed to multiple patient specific criteria. In another embodiment of the invention, hybrid ceramic material is added to the shoulder 18 so as to alter angulations 28a and 28b so as to conform the shoulder 18 to a patient specific criterion.

Once the shoulder 18 has been conformed to the necessary patient specific criteria, the shoulder 18 is finally cured 21. In one embodiment of the invention, the shoulder 18 is cured by placing the abutment system 10 in a typical dental heat curing unit 23 to a final temperature of about 100–110 degrees Celsius. One such dental heat curing unit is manufactured by Kuraray.

In an alternate embodiment of the present invention, in order to conform the shoulder 18 to the necessary patient specific criteria, it is necessary to add additional hybrid ceramic material to the shoulder 18 more than once. It may be necessary to add additional hybrid ceramic material to different areas on the shoulder 18 each time hybrid ceramic material is added, or hybrid ceramic material may be added to the shoulder 18 in the same area of the shoulder 18 each time. In another embodiment of the present invention, in order to conform the shoulder 18 to the necessary patient specific criteria, it is necessary to remove additional hybrid ceramic material from the shoulder 18 more than once. It may be necessary to remove additional hybrid ceramic material from different places on the shoulder 18 each time hybrid ceramic material is added, or hybrid ceramic material may be removed from the same area of the shoulder 18 each time. In still another embodiment of the invention, it may be necessary to alternatively add and remove hybrid ceramic material to the shoulder 18 in order to conform the shoulder 18 to the necessary patient specific criteria.

In another alternate embodiment, as shown in FIG. 1, after the shoulder 18 is finally cured, the shoulder 18 is polished 25. In a preferred embodiment of the invention, the shoulder 18 is polished using a series of polishing wheels 27. In a particularly preferred embodiment, the shoulder 18 is polished using a series of heavy grit, medium grit, and fine grit diamond impregnated silicone polishing wheels, and then polished to a high shine using a felt wheel and Kuraray Estenia® polishing compound.

Figure 3:
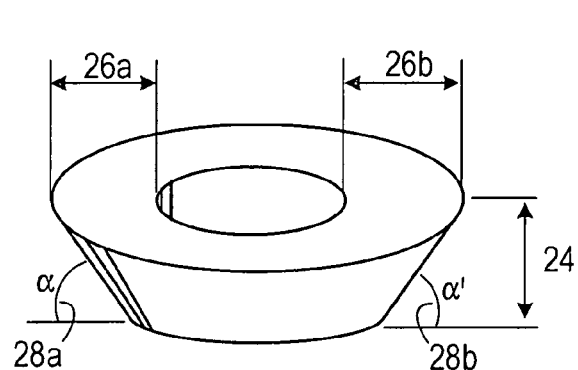
FIG. 3 is a front view of a shoulder as described herein.

As shown in FIG. 3, the shoulder 18 can be altered by adding or removing hybrid ceramic material to or from various dimensions of the shoulder 18. The height 24, widths 26a and/or 26b, and/or angulations 28a and/or 28b can all be adjusted.

Figure 5A:
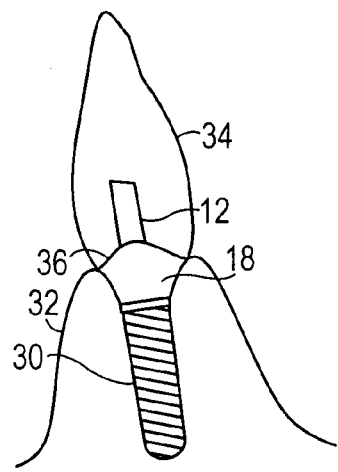
FIG. 5 is a front view of a placement of a dental implant, the present invention and a crown in relation to the gum tissue.
Figure 5B:
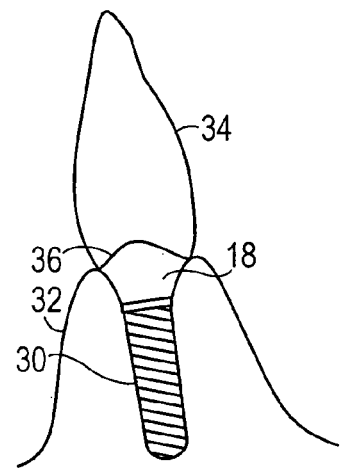
Figure 5C:
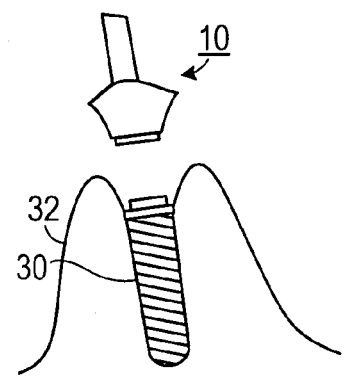

FIG. 5 shows the abutment system 10 as it is affixed to the dental implant 30 in relation to the gum tissue 32. The crown 34 is then affixed over the abutment system 10. The fit of the crown 34 to the shoulder 18 results in little to no margin 36 being visible.

Figure 2:
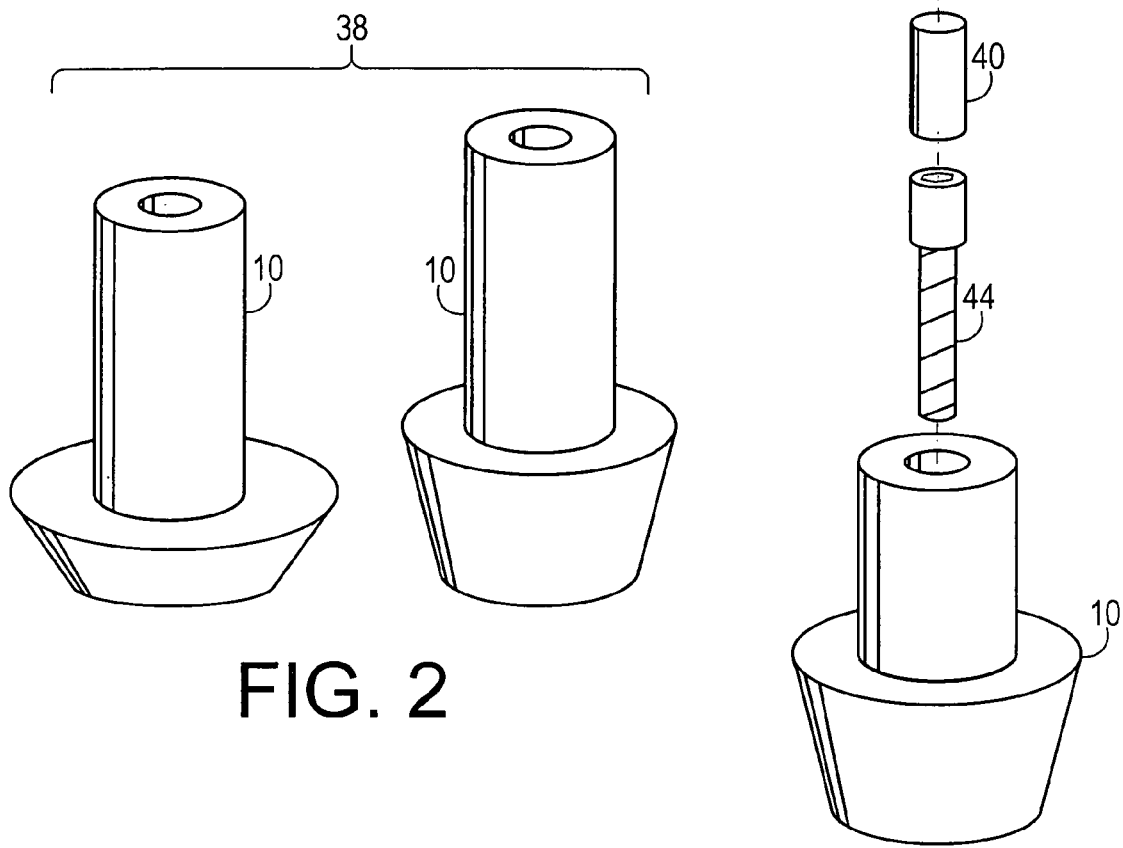
FIG. 2 is a view of a kit of abutment systems.

In another embodiment of the present invention, as shown in FIG. 2, a plurality of abutment systems 10 are located in a kit 38. Each abutment system 10 is manufactured according to a specific set of patient specific criteria, and then grouped in a kit 38 with all other abutment systems 10 that were manufactured according to the same specific set of patient specific criteria.

Figure 6:
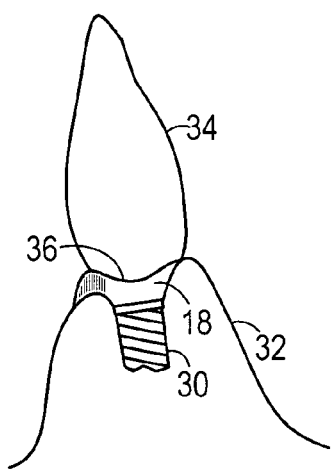
FIG. 6 is a front view of the present invention where pigment has been added to a portion of the hybrid ceramic shoulder.

In yet another alternative embodiment, shown in FIG. 6, pigment is added to an amount of hybrid ceramic material prior to adding that amount of hybrid ceramic material to the shoulder 18 so as to give the portion of the shoulder 18 extending outward over the gum tissue 32 the appearance of additional gum tissue.

Figure 4:
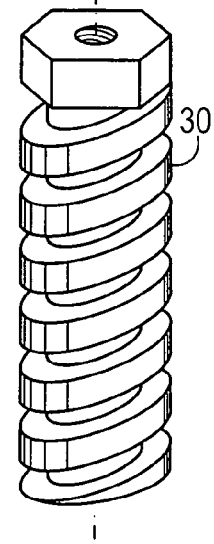
FIG. 4 is an exploded front view of an abutment system disclosed herein.

In yet another alternative embodiment, as shown in FIG. 4, an amount of hybrid ceramic material is formed into a plug 40 and is placed into the hollow portion 42 of the abutment 12. FIG. 4 shows how the abutment system 10 is affixed to the dental implant 30 by a screw 44. A plug 40 is then placed into the opening 42 of the abutment 12.

Another advantage of the present invention is the ability to place the abutment onto the fixture at the time of first stage placement surgery. This allows the abutment to function as the healing cap and model the tissue during the integration stage of healing. This also facilitates the use of a temporary crown over the abutment so as to create an immediate load environment. Immediate loading is extremely beneficial to the integration stage of the fixture into the bone, and is highly preferred by the patient, as the patient is able to leave the dentist's office with a temporary crown in place.

Another component of the present invention is the use of plastic try-in abutments to determine the correct size, shape and angulation of the permanent abutment. These plastic abutments are used by oral surgeons at the time of implant placement surgery, and the information gathered at that time allows the surgeon or restorative dentist to choose the most appropriate permanent abutment. These plastic try-in abutments can be manufactured from any plastic material. In a preferred embodiment, the plastic try-in abutments are manufactured from an autoclavable plastic material, which allows the dentist to sterilize the plastic try-in abutment and therefore use the plastic try-in abutments with more than one patient. In a particularly preferred embodiment, the plastic material that is used to manufacture the plastic try-in abutments is Delrin®, an acetal resin that is manufactured by DuPont. In addition to the plastic abutments, hybrid ceramic shells consisting of predetermined shapes and sizes that correspond to the various teeth are available to be placed directly onto the permanent abutment for the purpose of immediate temporization. This alleviates the time intensive procedure of fabricating temporaries in the traditional method. This provides the oral surgeon with the ability to select the correct permanent abutment at the time of first stage surgery. The final abutment can be determined and placed by utilizing a series of preformed try-in abutments to determine the angulation, tissue height, tissue emergence contour, margin height and overall size in relation to the hard and soft tissues. After placement of the permanent abutment, a temporary crown may also be placed by the oral surgeon. This creates a highly favorable environment known as immediate loading.

Another advantage of the present invention is the relative ease of temporization by utilizing pre-formed hybrid ceramic shells as temporary crowns placed on permanent abutment that are placed at the time of first stage surgery. The shells can be preliminarily tacked into place on the abutment to verify correct profile, angulation, occlusal contact, proximal contact, and emergence profile. The shells may be manufactured to any shape or size, so the shell may be in the location of anterior or posterior teeth, and may be used to represent the front, top or back of the tooth. After verification of required placement the shell is then filled in on the underside with additional hybrid ceramic material so as to fully adapt to the abutment. This facilitates extremely accurate and natural looking temporary crowns. This procedure is particularly favorable for immediate load temporization.

Figures 7A, 7B, 7C:
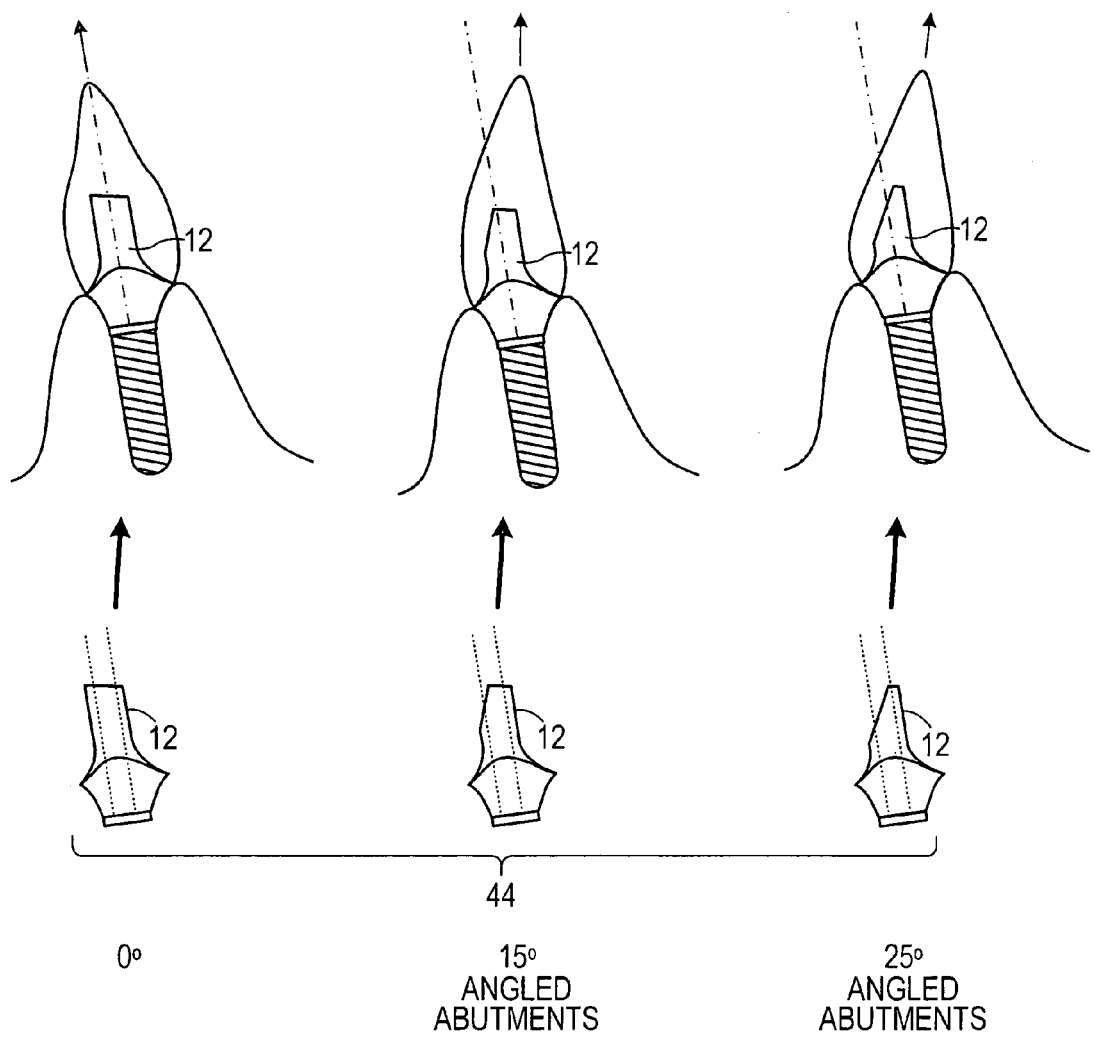
FIG. 7 is a front view of a kit of various angled try-in abutments.
Figure 8B:
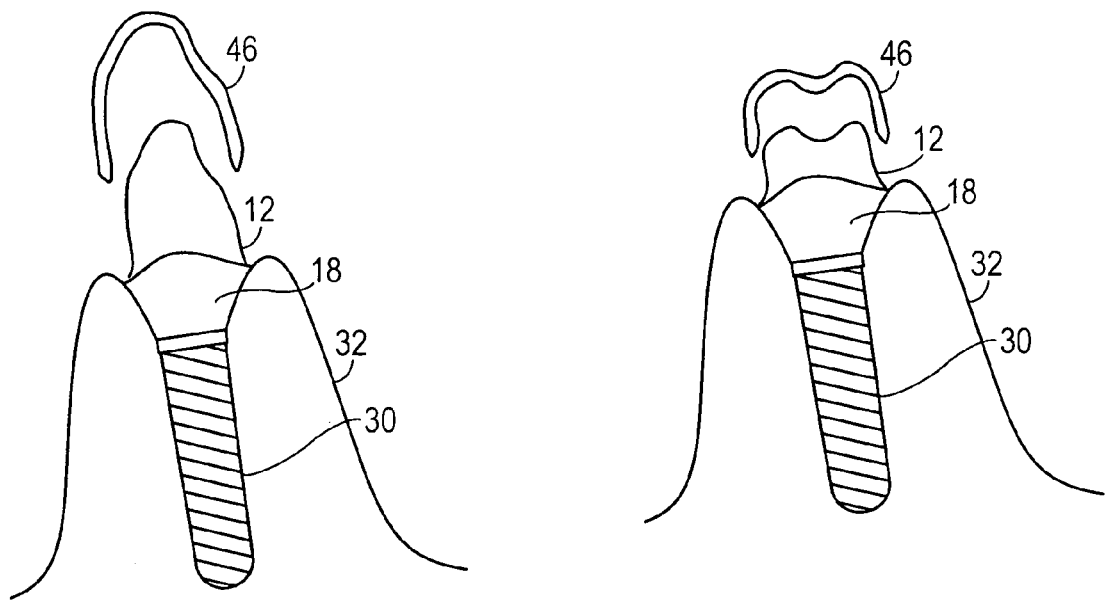
FIG. 8b is an exploded front view of hybrid ceramic shells affixed to try-in abutments.
Figure 8A:
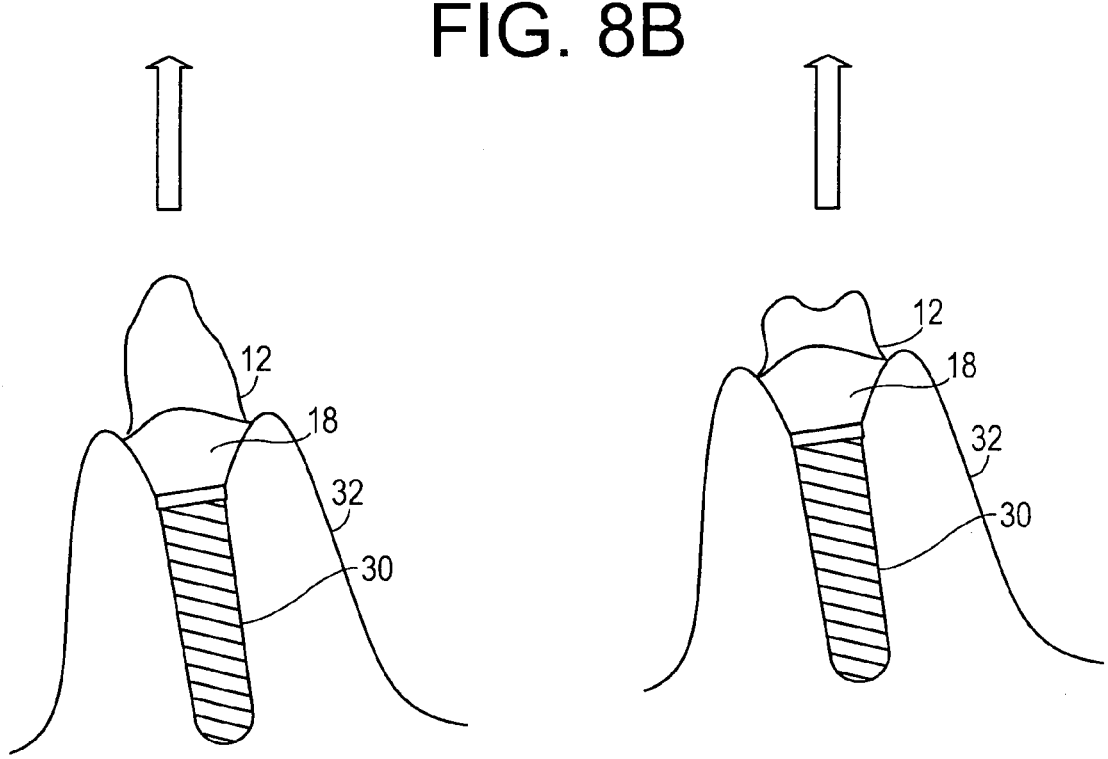
FIG. 8a is a front view of try-in abutments that have been affixed to dental implants.
Figures 9A, 9B:
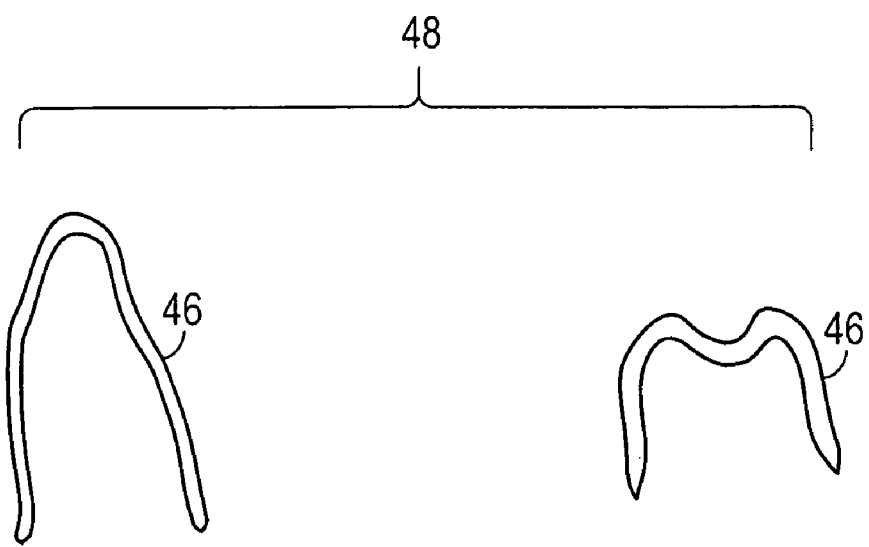
FIGS. 9a–9b are front views of a kit of hybrid ceramic shells.

In one embodiment of the present invention, the abutment 12 can be manufactured from an autoclavable plastic material to create a temporary plastic try-in abutment. As shown in FIG. 7, a plurality of plastic try-in abutments 12 are located in a kit 46. Each try-in abutment 12 is manufactured according to a specific set of patient criteria, and then grouped in a kit 44 with all other try-in abutments 12 that were manufactured according to the same specific set of patient specific criteria In another embodiment, as shown in FIGS. 8a and 8b, a hybrid ceramic shell 46 is affixed to an abutment 12. As shown in FIG. 9, a plurality of shells 46 are located in a kit 48. Each shell 46 is manufactured according to a specific set of patient criteria, and then grouped in a kit 48 with other shells 46 that were manufactured according to the same specific set of patient specific criteria.

The above-described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. A method of preparing an abutment system, comprising the steps of:
   a. forming a curable hybrid ceramic material into a shoulder about a base portion of an abutment, the abutment being an abutment configured for placement on a dental implant that has been implanted into a jawbone and configured to be removably affixed to the dental implant;
   b. partially curing the hybrid ceramic material so as to form an initially cured shoulder;
   c. after partially curing the hybrid ceramic material, shaping the initially cured shoulder to a desired shape so that the shoulder conforms to at least one patient specific criterion; and
   d. completely curing the shoulder.

2. The method of claim 1, further comprising the step of applying an opaque material to the abutment prior to forming the curable hybrid ceramic material into a shoulder about the base portion of the abutment.

3. The method of claim 1, wherein the step of shaping the initially cured shoulder to a desired shape so that the shoulder conforms to at least one patient specific criterion is performed by adding additional hybrid ceramic material to the initially cured shoulder.

4. The method of claim 1, wherein the step of shaping the initially cured shoulder to a desired shape so that the shoulder conforms to at least one patient specific criterion is performed by removing an amount of hybrid ceramic material from the initially cured shoulder.

5. The method of claim 1, wherein the step of shaping the initially cured shoulder to a desired shape so that the shoulder conforms to at least one patient specific criterion is performed by adding and removing hybrid ceramic material from the initially cured shoulder.

6. The method of claim 1, wherein the hybrid ceramic material comprises at least 85% porcelain.

7. The method of claim 6, wherein the hybrid ceramic material comprises 92% porcelain.

8. The method of claim 1, wherein the hybrid ceramic material further comprises a pigment.

9. The method of claim 1, wherein the partially curing step comprises subjecting the hybrid ceramic material to ultraviolet light.

10. The method of claim 1, wherein the completely curing step comprises subjecting the shoulder to heat.

11. The method of claim 10, wherein the shoulder is subjected to a temperature between about 100 degrees Celsius and about 110 degrees Celsius.

12. The method of claim 1, further comprising the step of polishing the shoulder.

* * * * *